United States Patent
Rezai et al.

(10) Patent No.: US 8,082,033 B2
(45) Date of Patent: Dec. 20, 2011

(54) SYSTEM AND METHOD FOR PROVIDING A WAVEFORM FOR STIMULATING BIOLOGICAL TISSUE

(75) Inventors: Ali R. Rezai, Bratenhal, OH (US); Nagi Hatoum, Cleveland Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 498 days.

(21) Appl. No.: 11/404,006

(22) Filed: Apr. 13, 2006
(Under 37 CFR 1.47)

(65) Prior Publication Data
US 2007/0000372 A1    Jan. 4, 2007

Related U.S. Application Data

(60) Provisional application No. 60/671,011, filed on Apr. 13, 2005.

(51) Int. Cl.
*A61N 1/04* (2006.01)
(52) U.S. Cl. .................................................. 607/2
(58) Field of Classification Search .............. 607/5, 45, 607/46, 30, 57, 59
See application file for complete search history.

(56) References Cited

U.S. PATENT DOCUMENTS

| | | | |
|---|---|---|---|
| 4,151,470 A * | 4/1979 | Sato ................................... 369/5 |
| 4,156,259 A * | 5/1979 | Sato ................................. 360/94 |
| 4,180,821 A * | 12/1979 | Prewitt et al. ..................... 346/7 |
| 4,424,812 A | 1/1984 | Lesnick |
| 4,543,955 A | 10/1985 | Schroeppel |
| 4,598,713 A | 7/1986 | Hansjurgens et al. |
| 4,651,740 A | 3/1987 | Schroeppel |
| 4,699,143 A * | 10/1987 | Dufresne et al. ................ 607/46 |
| 5,354,320 A * | 10/1994 | Schaldach et al. .............. 607/46 |
| 5,433,736 A | 7/1995 | Nilsson |
| 5,503,158 A * | 4/1996 | Coppock et al. .............. 600/508 |
| 5,607,460 A | 3/1997 | Kroll et al. |
| 5,891,178 A | 4/1999 | Mann et al. |
| 6,044,301 A * | 3/2000 | Hartlaub et al. ................ 607/31 |
| 6,208,896 B1 * | 3/2001 | Mulhauser ........................ 607/5 |
| 6,249,703 B1 * | 6/2001 | Stanton et al. ................. 607/30 |
| 6,263,246 B1 | 7/2001 | Goedeke et al. |
| 6,289,247 B1 * | 9/2001 | Faltys et al. ..................... 607/57 |
| 6,308,099 B1 | 10/2001 | Fox et al. |
| 6,354,299 B1 | 3/2002 | Fischell et al. |
| 6,418,346 B1 | 7/2002 | Nelson et al. |
| 6,516,227 B1 * | 2/2003 | Meadows et al. .............. 607/46 |
| 6,539,263 B1 | 3/2003 | Schiff et al. |
| 6,560,490 B2 | 5/2003 | Grill et al. |

(Continued)

FOREIGN PATENT DOCUMENTS

JP         10 216244 A      8/1998

OTHER PUBLICATIONS

Fisekovic et al., "New Controller for Functional Electrical Stimulation Systems", *Med. Eng. Phys.* 2001; 23:391-399.

(Continued)

*Primary Examiner* — Scott Getzow
*Assistant Examiner* — Amanda Patton
(74) *Attorney, Agent, or Firm* — Kenyon & Kenyon LLP (57) ABSTRACT

An implantable programmable stimulator system includes memory that stores waveform data for at least one waveform. A playback system provides at least one output waveform based on the waveform data.

41 Claims, 2 Drawing Sheets

U.S. PATENT DOCUMENTS

| | | |
|---|---|---|
| 6,587,724 B2 | 7/2003 | Mann |
| 6,609,031 B1 | 8/2003 | Law et al. |
| 6,622,045 B2 | 9/2003 | Snell et al. |
| 6,628,989 B1 | 9/2003 | Penner et al. |
| 6,654,642 B2 | 11/2003 | North et al. |
| 6,657,106 B2 * | 12/2003 | Smith et al. .................. 800/278 |
| 6,662,049 B1 | 12/2003 | Miller |
| 6,681,136 B2 * | 1/2004 | Schuler et al. .................. 607/44 |
| 6,714,812 B1 | 3/2004 | Karjalainen et al. |
| 6,731,986 B2 | 5/2004 | Mann |
| 6,775,573 B2 * | 8/2004 | Schuler et al. .................. 607/40 |
| 6,778,858 B1 * | 8/2004 | Peeters .......................... 607/57 |
| 6,804,558 B2 | 10/2004 | Haller et al. |
| 6,934,580 B1 * | 8/2005 | Osorio et al. .................. 600/545 |
| 7,308,302 B1 * | 12/2007 | Schuler et al. .................... 607/2 |
| 2003/0060860 A1 | 3/2003 | Foster et al. |
| 2003/0093129 A1 * | 5/2003 | Nicolelis et al. ................ 607/45 |
| 2003/0149457 A1 | 8/2003 | Tcheng et al. |
| 2003/0204221 A1 | 10/2003 | Rodriguez et al. |
| 2003/0204224 A1 | 10/2003 | Torgerson et al. |
| 2003/0204226 A1 | 10/2003 | Acosta et al. |
| 2003/0208244 A1 | 11/2003 | Stein et al. |
| 2004/0098067 A1 | 5/2004 | Ohta et al. |
| 2005/0251061 A1 * | 11/2005 | Schuler et al. ................ 600/545 |
| 2006/0239482 A1 * | 10/2006 | Hatoum ........................ 381/312 |
| 2007/0078498 A1 * | 4/2007 | Rezai et al. ..................... 607/59 |

OTHER PUBLICATIONS

Mouine et al., "Multi-Strategy and Multi-Algorithm Cochlear Prostheses", *Biomed. Sci. Instrument*, 2000; 36:233-238.

Voghell et al., "Programmable Current Source Dedicated to Implantable Microstimulators", *ICM '98 Proceedings of the Tenth International Conference*, pp. 67-70.

Mayr et al., "Basic Design and Construction of the Vienna FES Implants: Existing Solutions and Prospects for New Generations of Implants", *Medical Engineering &Physics*, 2001; 23:53-60.

McNaughtan et al., "Electrochemical Issues in Impedance Tomography", *1st World Congress on Industrial Process Tomography*, Buxton, Greater Manchester, Apr. 14-17, 1999.

* cited by examiner

SYSTEM AND METHOD FOR PROVIDING A WAVEFORM FOR STIMULATING BIOLOGICAL TISSUE

RELATED APPLICATION

This application claims the benefit of U.S. Provisional Patent Application No. 60/671,011, which was filed Apr. 13, 2005, and entitled SYSTEM AND METHOD FOR PROVIDING A WAVEFORM FOR STIMULATING BIOLOGICAL TISSUE, the entire contents of which is incorporated herein by reference.

TECHNICAL FIELD

The present invention relates generally to a system and method for providing a waveform for stimulating biological tissue.

BACKGROUND

Various types of stimulators have been developed for a variety of in-vivo applications. For example, a stimulator can be employed for performing spinal cord stimulation, deep-brain stimulation or for stimulation of other neurological paths, such as for treatment of various disorders and diseases. Typically, each stimulator includes a waveform generator that generates its own waveform. For instance, a user defines the necessary parameters and the stimulator constructs the waveform accordingly. Usually the parameters include amplitude, frequency, phase symmetry and duty cycle. The more complex the waveform, the more parameters are necessary to describe the waveform.

Implantable stimulators are constrained by space and typically cannot accommodate complex circuitry. Implantable stimulators, therefore, usually trade off waveform complexity for saving space. A simpler stimulator design also tends to consume less power, which is also a significant consideration in implantable devices. For example, power saving is important since surgery is usually required to replace the battery. Furthermore, simple stimulator designs are rugged and are generally less prone to failure. Safety and low failure rate are important requirements by the government regulator agencies for approving any medical device.

SUMMARY

The present invention relates generally to a system and method for providing a waveform for stimulating biological tissue.

One embodiment of the present invention provides an implantable programmable stimulator system that includes memory that stores waveform data for at least one waveform. A playback system provides at least one output waveform based on the waveform data.

Another embodiment of the present invention provides an implantable pulse generator (IPG). The IPG includes memory that stores a waveform representation for each of a plurality of waveforms. A playback system is configured to retrieve at least one of the stored waveform representations from the memory and to provide at least one corresponding output waveform signal. At least one amplifier amplifies the corresponding output waveform signal to provide a corresponding amplified output waveform signal.

Yet another embodiment provides a method for providing a waveform for stimulation of biological tissue. The method includes storing non-parametric waveform data corresponding to a plurality of recorded waveforms in memory located in an implantable pulse generator. At least one of the plurality of waveforms is retrieved from the memory. An output waveform is provided from playback circuitry located in the implantable pulse generator, the output waveform corresponding to the at least one of the plurality of waveforms retrieved from the memory.

DETAILED DESCRIPTION

The present invention relates to an implantable programmable stimulation system that can provide an output waveform, such as for use in stimulating biological tissue. The system includes memory that stores waveform data that represents one or more waveforms. The waveforms can be generated externally and provided to the memory. The system also includes a playback system, which can be similar to electronic digital or analog sound recording and playback devices. The playback system provides an output waveform based on the waveform data. For instance, one or more selected waveforms can be selected and played back via the playback system to provide an output waveform to an amplifier. The amplifier amplifies the output waveform (e.g., using voltage or current control) to stimulate the biological tissue electrically. For example, the amplified output waveform can be provided to an electrode implanted at a location for delivering the electrical stimulus to targeted biological tissue (e.g., target sites within the brain, spinal cord, or heart). The output waveform can be adjusted or modified.

Figure 1:
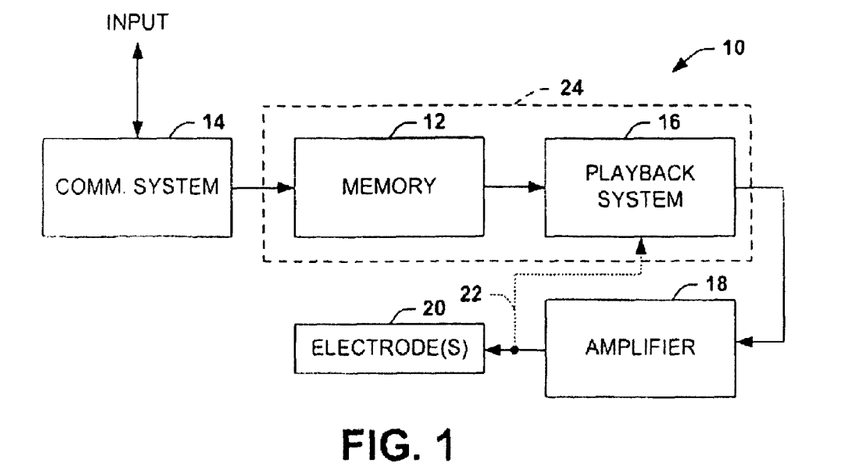
FIG. 1 depicts an example of a block diagram for a programmable stimulation system that can be implemented according to an aspect of the present invention.

FIG. 1 depicts a stimulation system 10 that can be implemented according to an aspect of the present invention. The stimulation system 10 includes memory 12 that stores (or records) waveform data corresponding to one or more waveforms. The waveform data can be preprogrammed, such as prior to implantation, or the waveform data can be programmed post-implantation of the system 10. The waveform data can be stored in the memory 12 based on an INPUT signal received by a communication system 14. The one or more waveforms can be stored as one or more complete periods of the waveform, which can be referred to as snippets. As described herein, the waveform data that is stored in the memory 12 corresponds to one or more actual waveforms, which can be an analog or digital representation of the waveform(s). This type of waveform data that is stored in the memory 12 is referred to herein as non-parametric waveform data.

The communication system 14 can include a receiver that receives the INPUT signal via one or more communication modes, such as including radio frequency (RF), infrared (IR), direct contact (e.g., electrically or optically conductive path), capacitive coupling, and inductive coupling to name a few. The INPUT signal further can be provided via more than one communication mode, such as providing the INPUT signal as including one or more waveforms via one mode and command information (e.g., scheduling and programming information) via another mode. The communication system 14 can be capable of bi-directional communications, such as also including a transmitter or transceiver circuitry. The transmitter and receiver portions of the communication system 14 can employ the same or different communication modes.

The memory 12 can be implemented as an analog memory, such as is capable of storing an analog version of the waveform that is received by the communication system 14. The memory can also be implemented as digital memory that stores a digital representation or sample of the input waveform or stores a digitally encoded version of the waveform. For instance, the memory 12 can store the sample waveform as a digital sample, such as using pulse code modulation (PCM) or adaptive differential pulse code modulation (ADPCM) or pulse width modulation (PWM), although other modulation techniques can be utilized. The digital sample of the waveform further may be stored in a compressed format according to one or more CODECs (e.g., MP3, AAC, 3GPP, WAV, etc.), although compression is not required. There are a multitude of varying standards that can be grouped in three major forms of audio CODECs, including, for example, direct audio coding, perceptual audio coding, and synthesis coding, any one or more of which can be employed to store a digital representation of waveforms in the memory 12.

A playback system 16 is configured to retrieve and play back one or more waveforms according to selected waveform data stored in the memory 12. The playback system 16 can be implemented as hardware (e.g., one or more integrated circuits), software or a combination or hardware and software. The implementation of the playback system 16 can vary, for example, according to the type of audio (analog or digital) that is stored in the memory 12. The playback system 16, for example, can be programmed with one or more audio CODECs that convert (or decode) the encoded waveform data into a corresponding output waveform.

The playback system 16 can be implemented as an integrated circuit 24, such as including a microcontroller or microprocessor. For instance, suitable microcontroller integrated circuits (ICs) are commercially available from Atmel Corporation of San Jose, Calif. Such microcontroller ICs may include the memory 12 integrated into the IC 24, such as in the form or FLASH memory or other programmable memory (electrically programmable read only memory (EPROM)), or the memory 12 can be external to the IC 24.

The playback system 16 provides the output waveform to an amplifier 18 that amplifies the output waveform. The playback system 16 further can be configured to provide output waveforms to one or more output channels, each output channel providing an amplified output waveform corresponding to the waveform data stored in the memory 12. One or more electrodes 20 can be coupled to each of the channels for delivering electrical stimulation to biological tissue located adjacent the electrode(s).

As an example, the playback system 16 can be configured to select one or more waveforms from the memory 12 for providing a corresponding output waveform. As mentioned above, a plurality of different types of waveforms can be stored in the memory 12, generally limited only by the size of the memory. The playback system 16 thus can select and arrange one or more waveforms to provide a desired output waveform pattern. Additionally, the playback system 16 further can combine a plurality of different waveforms into more complex composite output waveforms. It will be appreciated that the ability of selecting from a plurality of predefined stored waveforms affords the stimulation system enhanced capabilities, as virtually any output waveform can be stored and played back from the memory 12.

The design can be simplified even further by storing waveforms of gradually changing parameters in the memory 12. For example, a plurality of versions of the same waveform, but of varying amplitude, can be stored in the memory 12 so as to effectively eliminate the need for additional amplitude controlling circuitry. Accordingly, if a greater or lesser amplitude may be required for a given application, an appropriate different waveform can be selected. The playback system 16 can also be programmed and/or configured to manipulate one or more selected waveforms from the memory 12, such as using digital or analog computation, to vary parameters (e.g., amplitude, frequency, phase symmetry and/or duty cycle) of the one or more selected waveforms. The corresponding amplified output signal corresponds to an amplified version of the selected waveform, including any such manipulations.

The amplifier 18 can be implemented as an analog amplifier or a digital amplifier. For an analog version of the amplifier 18, a digital-to-analog converter (not shown) can provide a corresponding analog version of the output waveform and a linear amplifier can, in turn, operate to amplify the analog output waveform to a desired level. Power conditioning circuitry can be utilized to provide a desired potential for use in generating the amplified output waveform. Alternatively, the amplifier can be implemented as a class D amplifier (or switched power supply), although other amplifier topologies can also be used. By implementing the amplifier as a class D amplifier, the amplifier 18 can run directly off a battery or other power supply efficiently and be implemented using low-voltage components. Those skilled in the art will appreciate various types of switching amplifier topologies are that can be utilized in the system 10. Additionally, the amplifier 18 can be configured to operate in a current mode or a voltage mode control, such as to provide a desired current or voltage.

The amplifier 18 can comprise a network of amplifiers arranged to drive a plurality of loads (depicted as electrodes 20) according to respective output waveforms provided by the playback system 16. The electrode(s) 20 can be implanted in strategic locations in the patient's tissue according to given application of the stimulation system 10. For example, the electrode(s) can be located within a patient's brain, spinal cord or other anatomic locations. The anatomic locations can be in close proximity to the playback system or at remote locations.

The system 10 can be implemented as an open loop system or a closed loop system. For the example of a closed loop system, the system 10 can also include feedback, indicated as dotted line 22. The feedback 22 provides information about the stimulus being applied to the electrode(s) and/or about a characteristic of the electrode(s). As an example, the feedback 22 can provide an electrical signal to the playback system 16, based on which an indication of load impedance associated with the electrode(s) can be determined.

The impedance characteristics can be utilized for a variety of purposes. For instance, the impedance can be employed to implement current control, such as by the playback system 16 selecting a predefined waveform from the memory 12 to maintain a desired current level in the waveform that is provided to the electrode(s) 20. Alternatively or additionally, the impedance characteristics can be used as part of diagnostics, such as by recording (or logging) impedance over extended periods of time and evaluating a condition of the electrode(s). As another alternative, the feedback 22 can be employed to ascertain high impedance conditions (e.g., an open circuit) or a low impedance condition (e.g., a short circuit). Those skilled in the art will understand and appreciate various approaches that can be implemented to provide the feedback 22. Additionally, various types of diagnostic or operational controls can be implemented based on such feedback.

Since the waveform is played back from non-parametric waveform data that is stored in the memory 12, the system 10 can be implemented in a cost efficient manner from commercially available recording and playback circuitry. Additionally, because the waveforms can be generated externally, provided to the system 10, and stored in the memory 12, there is a greater degree of flexibility in the types and complexity of waveforms that can be stored in the memory. That is, the system 10 is not constrained by limitations in the cost or size or complexity of a typical parametric waveform generator. Additionally, the playback system 16 may further construct more complex waveforms by combining two or more stored waveforms in a particular order (e.g., a pattern of waveform trains). As an example, one or more of the waveforms stored in the memory can include actual recorded impulses (electrical waveforms), such as can be recorded from the patient in which the stimulation system 10 is to be implanted, from a different person or from a non-human animal subject.

Figure 2:
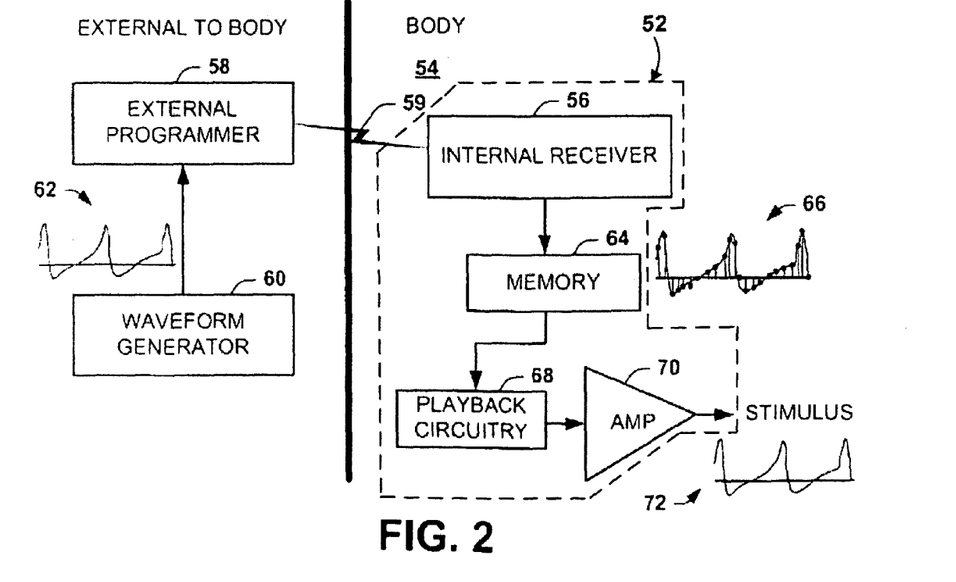
FIG. 2 depicts an example of yet another stimulation system that can be implemented according to an aspect of the present invention.

FIG. 2 depicts an example of a programmable stimulation system 50 that can be implemented according to an aspect of the present invention. The system 50 comprises an implantable pulse generator (IPG) 52 that is implanted in a patient's body 54, such as implanted under the skin of the chest (e.g., below the collarbone) or other anatomic location. In contrast to many existing IPG designs, the IPG 52 is not required to generate a pulse or waveform, but instead is configured to play back one or more predefined waveforms. The IPG 52 includes an internal receiver 56 that can receive a signal from an external programmer 58, which is located external to the body 54. The external programmer 58 can communicate the signal to the receiver 56 using one or more communications modes, such as described herein. In the example, of FIG. 2, a connectionless communications mode is illustrated, although a physical connection can be made to provide an electrical or optical conductive medium for data communications.

A waveform generator 60 can provide one or more waveforms 62 to the external programmer 58 for transmission to the IPG 52. The waveform generator 60 can include any type of device or system that can generate the one or more waveforms 62, including a programmable signal generator, a pulse generator, and a waveform synthesizer to name a few. The waveform generator 60 further may be a PC-based system or a stand alone system capable of generating one or more desired waveforms. The waveform generator 60 can also be programmed with biological, recorded waveforms, such as may have been measured and recorded from the patient's body 54 or from any other biological subject (e.g., human or other animal).

For electrical stimulation of a patient's brain, the waveform can be recorded as electrical impulses measured from one or more anatomical regions of a biological subject's brain. The waveform generator 60 thus can provide the biological, recorded waveforms to the external programmer 58 for transferring such waveforms to the memory via the internal receiver 56 of the IPG 52. The measurements, for example, can be made by sensing electrodes inserted within target tissue or by external sensors placed adjacent target tissue or a combination of internal or external sensors. Those skilled in the art will understand and appreciate various types of sensors and measurement devices that can be employed to measure and record the biological waveforms. Additionally, while the foregoing mentions recording electrical impulses from one or more regions of a subject's brain, it is to be appreciated that the impulses can be recorded from other nerve tissue, one or more other organs, or other anatomical sites (human or other animal) or any combination thereof.

The external programmer 58 transmits a signal 59 to the receiver 56 of the IPG 52 corresponding to the waveform 62 provided by the generator 60. As discussed herein, the signal 59 transmitted by the external programmer 58 can include (or encode) the actual waveform 62 provided by the waveform generator 60 (e.g., an actual biological, recorded waveform or a synthesized waveform). The external programmer can transmit the signal 59 as including a complete period, more than one period (e.g., snippets) or as a fraction of a period of the desired waveform 62 in any communications mode. The receiver 56, for example, can provide the waveform to the memory as encoded waveform data, such as corresponding to an encoding scheme implemented by the waveform generator 60. Alternatively, the receiver 56 can demodulate/decode an encoded received signal and provide a corresponding demodulated/decoded signal 66 to the memory 64 so that the waveform data corresponds to the one or more waveforms 62. Additionally encoding may also be performed by the receiver 56 or other circuitry (not shown) for providing encoded waveform data for storing the waveform(s) 62 the memory 64.

The sample of the waveform 66 stored in the memory 64 can correspond to an analog version of the waveform or a corresponding digital (e.g., PCM) representation of the waveform. Those skilled in the art will appreciate various different representations that can be stored in the memory 64 based on the teachings contained herein. It will further be understood that some or all of the waveforms 66 stored in the memory 64 can be programmed prior to implantation of the IPG 52 within the body 54.

After a desired number of one or more waveforms 66 have been stored in the memory 64, such as during a program mode, playback circuitry 68 can play back one or more selected waveforms 66 from the memory 64. The playback circuitry 68 can play back a waveform according to a defined play back schedule, which may be a periodic or continuous schedule. Alternatively or additionally, the playback circuitry 68 can be configured to play back one or more selected waveforms in response to a stimulus, which stimulus can be user-generated or provided by associated sensing circuitry (not shown).

The playback circuitry 68 can play back the one or more selected waveforms by retrieving the selected waveform(s) from the memory and providing the output waveform(s) to one or more amplifiers 70. The amplifier 70 amplifies the output waveform to a desired level to provide a corresponding amplified version of the waveform. That is, the amplified waveform 72 can be substantially the same as the waveform 62 generated by the waveform generator 60. Alternatively, when the waveform 62 is stored as encoded data, the amplified waveform 72 can correspond to a decoded version of the waveform. Typically, a plurality of waveforms 66 are stored in the memory 64 to provide a greater selection of available waveforms for operating the IPG 52. The amplified waveform 72 can be provided to one or more strategically placed electrodes or other implantable devices capable of delivering an electrical stimulus to adjacent biological tissue.

Figure 3:
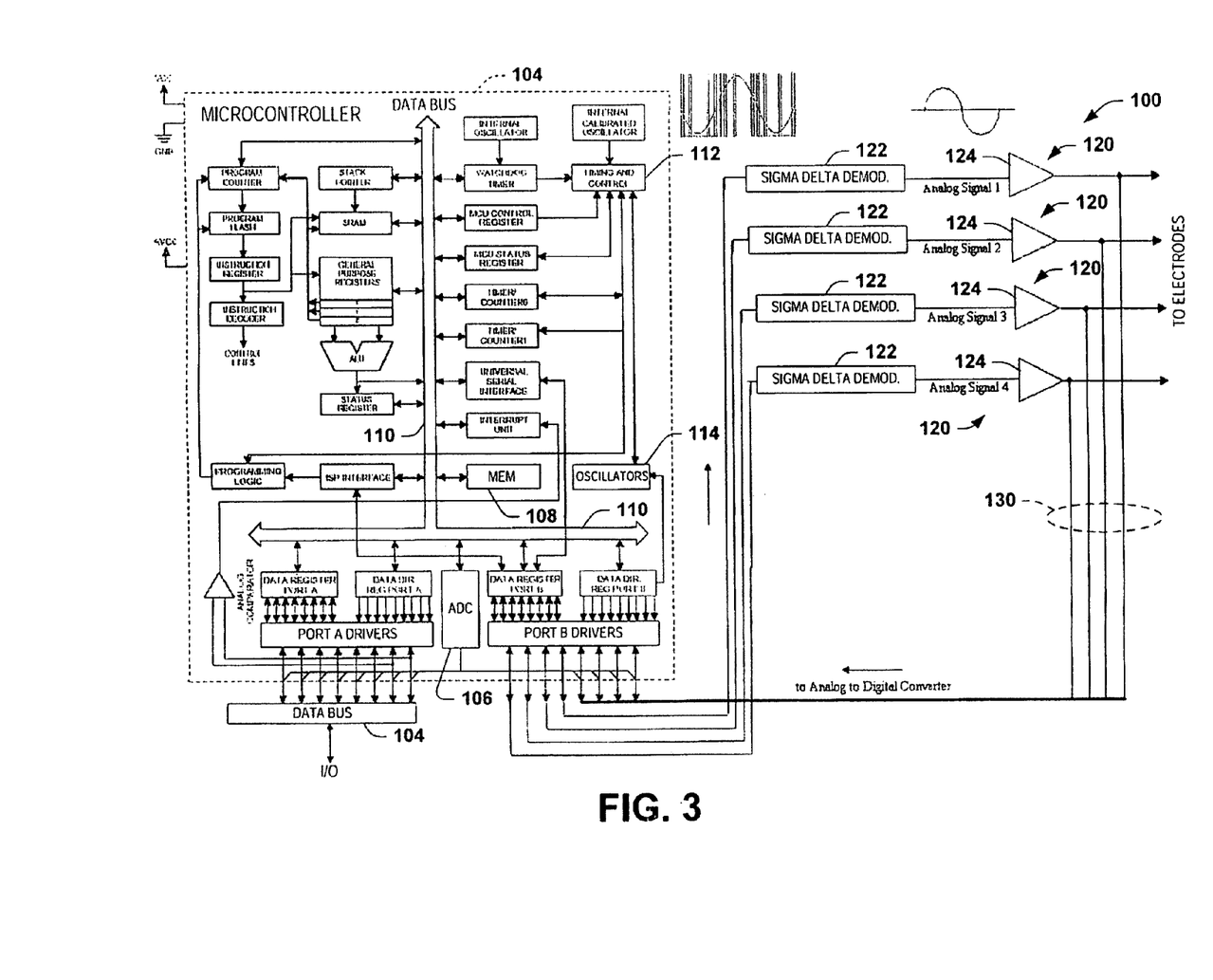
FIG. 3 depicts an example of a stimulation system with external programming implemented according to an aspect of the present invention.

FIG. 3 depicts an example of part of a microprocessor based stimulation system 100 that can be implemented according to an aspect of the present invention. The system 100 includes a microcontroller 102 that is programmed and/or configured to control the system. The microcontroller 102 can communicate with an external device via a data bus 104. The data bus 104 can provide for bi-directional communication relative to the microcontroller 102. The communication may include input and/or output (I/O) data, such as provided by a communications system (e.g., a transmitter or receiver, not shown). The I/O data can be analog or digital data, as the microcontroller 102 includes an analog-to-digital converter 106.

By way of example, the I/O data can include command data and waveform data. The command data can include scheduling information that controls operation of the system 100. For instance, the scheduling information can identify which waveform(s) is to be played, how many times the waveform is to be played (e.g., a fixed number or continuously). The command data thus can be employed to program one or more registers or other types of memory with program instructions or operating parameters to control operation of the system 100. The command data may also be utilized to enter a programming or learning mode, such as during which waveform data can be learned or programmed into the system 100. The command data can also be provided as part of a diagnostic mode in which information about system operation can be obtained from the system 100 as output data.

The waveform data can correspond to any number of one or more sample waveforms, which can be stored in memory 108 of the microcontroller 102. While the memory 108 is depicted as being internal to the microcontroller 102, the memory could be external to the microcontroller or be distributed partially within the microcontroller and partially external. The memory 108 can be implemented as programmable memory, such as including FLASH memory, EPROM or other memory types. The memory 108 and other components of the microcontroller 102 (as depicted in FIG. 3) can be accessed via an internal bus 110.

The microcontroller 102 includes a timing and control block 112 that controls an oscillator 114 to provide a corresponding digital waveform to one or more associated port drivers 116. The one or more port drivers 116 can receive more than one waveform (e.g., via a register 118) from the oscillator 114, each of which corresponds to one or more waveforms selected from the memory 108. In the example of FIG. 3, it is assumed that the waveforms stored in the memory 108 are digital waveforms, such as can be encoded according to any desired CODEC. The one or more port drivers 116 provide a corresponding output waveform to an associated output stage 120.

Each output stage 120 can include a digital-to-analog converter and an amplifier that provides a respective amplified output waveform. N output stages are utilized to provide N corresponding amplified output waveforms, where N is a positive integer (N≧1). In the example of FIG. 3, each of the output stages 120 includes a sigma delta demodulator 122 that demodulates the encoded data provided by the port drivers 116 and converts the digital representation to an analog signal. For instance, the waveforms stored in the memory 108 can be encoded as 1-bit sigma delta modulated signals, which allows for high resolution waveform reproduction with low noise without requiring digital compression. It is to be appreciated that other forms of demodulation, with or without compression, can also be utilized in the system 100. Each demodulator 122 provides a corresponding demodulated, analog output signal to an associated amplifier 124. Each amplifier 124 can drive an associated electrode with a corresponding amplified analog output signal (the amplified output signals indicated as being provided "to electrodes").

As an alternative, each output stage 120 can be configured to directly convert the digital output waveforms provided by the port drivers 116 to corresponding amplified analog signals. For example, the port drivers 116 could provide the output waveforms as PCM or PWM output waveforms. The output stages can include associated amplifiers, such as implemented as class D or switching amplifiers, which convert the digital output waveforms to corresponding amplified analog output waveforms. Those skilled in the art will understand and appreciate various types of switching amplifier topologies that could be implemented to provide a switching output signals based on such output waveforms. Thus, the averaged (or low-pass filtered) amplified output signal for each output stage represents a desired amplified output waveform. Those skilled in the art will understand and appreciate various possible amplifier topologies that can be utilized in the system 100 of FIG. 3 (as well as in the other approaches of FIGS. 1 and 2).

The system 100 can also employ feedback 130 for use in impedance determination and charge balancing using the techniques mentioned herein. For example, the feedback 130 can include an analog indication of electrode voltages, which are provided to the ADC 106 of the microcontroller 102 and converted to corresponding digital signals. The microcontroller 102 thus can employ the signals provided by the feedback information provided by the ADC to implement desired controls (e.g., voltage control or current control) or to implement diagnostic functions, such as described herein.

Various feedback schemes can be utilized to measure impedance characteristics of a load (e.g., electrode) that is associated with each of the respective output stages 120. The impedance characteristics can be described according to a model of an implanted electrode, such as may describe an electrode-electrolyte interface that is expressed as a serial capacitance and a serial resistance, together with a Faradic resistance in parallel with the series resistance and capacitance. Thus, the feedback scheme can be configured to measure the electrode model parameters in real time. Possible feedback schemes that could be implemented include a positive feedback scheme, a current interrupt scheme or continuous impedance measurement using small signal injections of multi-sinusoidal waveforms. Those skilled in the art will understand and appreciate various types of feedback schemes that can be utilized in accordance with the present invention.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the spirit and scope of the appended claims.

What is claimed is:

1. An implantable programmable stimulator system, comprising:
a processor configured to operate the implantable programmable stimulator system in a plurality of modes, wherein each mode is selected using command data that programs the stimulator system to operate in the respective mode, the processor comprising:
memory containing the command data and non-parametric waveform data for the at least one waveform preprogrammed to achieve electrical stimulation of the brain; and
a playback system programmed to play back the non-parametric waveform data for the at least one preprogrammed waveform as at least one output waveform; and
at least one electrode in electrical communication with the playback system and programmed to receive the at least one output waveform and deliver an electrical pulse to stimulate the brain using the at least one output waveform, wherein responsive to first command data corresponding to a first mode, the processor stores non-parametric waveform data received by a data bus into the memory, and wherein responsive to second command data corresponding to a second mode, the processor selectively retrieves non-parametric waveform data to provide to the playback system.

2. The system of claim 1, wherein the waveform data comprises non-parametric waveform data corresponding to at least a fraction of a period of the at least one waveform.

3. The system of claim 1, wherein the non-parametric waveform data further comprises non-parametric waveform data for a plurality of different waveforms, the playback system playing back the non-parametric waveform data for at least one of the plurality of different waveforms as the at least one output waveform.

4. The system of claim 3, wherein the processor is configured to construct the output waveform by combining at least two of the plurality of different waveforms contained in the memory.

5. The system of claim 1, wherein the waveform data is encoded according to a CODEC, the playback system being operative to decode the waveform data according to the CODEC to play back the waveform data as the output waveform.

6. The system of claim 1, further comprising an amplifier that provides an amplified output signal corresponding to the output waveform.

7. The system of claim 6, wherein the amplifier comprises a switching amplifier that provides the amplified output signal as a pulse-width-modulated signal.

8. The system of claim 6, wherein the at least one electrode receives the amplified output signal and emits an electrical stimulation signal having desired waveform characteristics according to the amplified output signal.

9. The system of claim 8, further comprising feedback from an output of the amplifier to the processor, the feedback providing the processor with information about at least one of the electrical stimulation signal emitted by the at least one electrode or a characteristic of the electrode.

10. The system of claim 1, wherein the playback system is at least one of programmed and configured to manipulate the output waveform to vary at least one parameter of the output waveform.

11. The system of claim 1, wherein a receiver receives an input signal that comprises the at least one waveform, the waveform data being stored in the memory according to the input signal to enable the playback system to play back at least a portion of the at least one waveform as the output waveform.

12. The system of claim 11, further comprising an external transmitter that provides the input signal according to at least one communication mode.

13. The system of claim 12, further comprising a waveform generator that provides the external transmitter with the at least one waveform, the external transmitter providing the input signal to program the memory with the waveform data for the at least one waveform.

14. The system of claim 13, wherein the waveform generator is programmed with at least one biological recorded electrical waveform, the waveform generator providing the at least one biological recorded waveform to the external transmitter, the input signal provided by the external transmitter comprising the at least one biological recorded electrical waveform.

15. The system of claim 12, wherein the memory and the playback system form part of a single integrated circuit that is separate from the external transmitter.

16. The system of claim 1, wherein the playback system is configured to play back at least one selected waveform from the memory according to a defined schedule.

17. The system of claim 1, wherein the playback system is configured to play back at least one selected waveform from the memory in response to a physiological stimulus to provide a corresponding electrical waveform.

18. The system of claim 1, wherein the memory contains waveform data for a plurality of waveforms, at least one of the plurality waveforms comprising a biological electrical waveform recorded from a biological subject.

19. The implantable programmable stimulator system of claim 1, wherein the at least one waveform is a train of waveform pulses.

20. The implantable programmable stimulator system of claim 19, wherein the train of waveform pulses is arranged in a predetermined order, and wherein each waveform pulse is one of the at least one preprogrammed waveform and an aggregate waveform combined from at least two of the at least one waveform.

21. The implantable programmable stimulator system of claim 1, wherein responsive to third command data corresponding to a third mode, the processor obtains feedback diagnostic information about the system.

22. An implantable programmable stimulator system, comprising:

a processor configured to operate the implantable programmable stimulator system in a plurality of modes, wherein each mode is selected using command data that programs the stimulator system to operate in the respective mode, the processor comprising:

memory containing command data and non-parametric waveform data representing for the at least one electrical waveforms pre-programmed to achieve predetermined electrical stimulation of the brain; and a playback system configured to retrieve at least one of the stored waveform representations from the memory and to play back the retrieved at least one waveform representation as at least one corresponding output waveform signal;

at least one amplifier that amplifies the at least one corresponding output waveform signal to provide at least one corresponding amplified output waveform signal; and at least one electrode in electrical communication with the at least one amplifier and programmed to receive the at least one corresponding amplified output waveform signal and deliver an electrical pulse to stimulate the brain using the at least one corresponding amplified output waveform, wherein responsive to first command data corresponding to a first mode, the processor stores non-parametric waveform data received by a data bus into the memory, and wherein responsive to second command data corresponding to a second mode, the processor selectively retrieves the at least one of the stored waveform representations from the memory to provide to the playback system.

23. The implantable pulse generator of claim 22, wherein a receiver receives a signal corresponding to at least one waveform according to a predetermined communication mode, the memory storing at least some of the stored waveform representations based on the signal received by the receiver.

24. The implantable pulse generator of claim 22, wherein the playback system is configured to retrieve and play back at least one selected waveform from the memory in response to a stimulus, such that the output waveform signal played back by the playback system comprises the at least one selected waveform for the electrical stimulation of biological tissue.

25. The implantable pulse generator of claim 22, wherein the playback system is configured to retrieve and play back at least one selected waveform from the memory according to a schedule, such that the output waveform signal played back by the playback system comprises the at least one selected waveform.

26. The implantable pulse generator of claim 22, wherein the memory and the playback system form part of a single integrated circuit.

27. The implantable pulse generator of claim 22, wherein the at least one electrode is electrically connected with the at least one amplifier, the at least one electrode emitting an electrical stimulation signal having waveform characteristics according to the corresponding amplified output waveform signal.

28. The implantable pulse generator of claim 27, further comprising feedback connected to provide the processor with information about at least one of the electrical stimulation signal emitted by the at least one electrode or a characteristic of the electrode.

29. The implantable pulse generator of claim 22, wherein the processor is configured to construct the at least one corresponding output waveform signal by combining at least two of the plurality of waveform representations stored in the memory.

30. The implantable pulse generator of claim 22, wherein the processor is at least one of programmed and configured to manipulate at least one of the plurality of waveforms retrieved from the memory so as to vary at least one parameter of the corresponding output waveform signal.

31. The implantable pulse generator of claim 22, wherein a receiver receives an input signal that is provided according to at least one communication mode, at least one waveform representation being stored in the memory according to the input signal.

32. The implantable pulse generator of claim 31, further comprising an external transmitter that provides the input signal according to the at least one communication mode.

33. The implantable pulse generator of claim 32, further comprising a waveform generator that provides the external transmitter with at least one of the plurality of waveforms, the external transmitter providing the input signal to program the memory with the waveform representation for the at least one of the plurality of waveforms provided by the waveform generator.

34. The implantable pulse generator of claim 33, wherein the waveform generator is programmed with waveforms recorded from a biological subject, the at least one of the plurality of waveforms provided by the waveform generator comprising at least one of the biological recorded electrical waveforms.

35. The implantable pulse generator of claim 22, wherein the memory contains a plurality of waveforms, at least one of the plurality waveforms contained in the memory comprising a biological electrical waveform recorded from a biological subject.

36. The implantable pulse generator of claim 22, wherein the plurality of waveforms contained in the memory as digital data and the playback system plays back the at least one corresponding output waveform signal as a digital output waveform signal, the implantable pulse generator further comprising a digital-to-analog converter that converts the digital output waveform signal to a corresponding analog output waveform signal, the amplifier comprising analog amplifier that amplifies the analog output waveform signal to provide the at least one corresponding amplified output waveform signal.

37. The implantable programmable stimulator system of claim 22, wherein responsive to third command data corresponding to a third mode, the processor obtains feedback diagnostic information about the system.

38. A method for electrically stimulating a brain, the method comprising:
    implanting an implantable programmable stimulator in a patient's body, the implantable programmable stimulator programmed to operate in a plurality of modes, wherein each mode is selected using command data that programs the stimulator system to operate in the respective mode, the stimulator having a processor and at least one electrode programmed to deliver an electrical signal to a brain, the processor comprising memory and a playback system, the memory containing the command data and non-parametric waveform data corresponding to at least one waveform preprogrammed to electrically stimulate the brain;
    responsive to first command data corresponding to a first mode, storing non-parametric waveform data received by a data bus into the memory; and
    responsive to second command data corresponding to a second mode:
        selectively retrieving the at least one waveform;
        playing back the selected at least one waveform as an output waveform; and
        delivering an electrical signal to the brain corresponding to the output waveform via the at least one programmed electrode.

39. The method of claim 38, further comprising, responsive to third command data corresponding to a third mode, obtaining feedback diagnostic information about the stimulator.

40. An implantable programmable stimulator system, comprising:
    a processor configured to operate the implantable programmable stimulator system in a plurality of modes, wherein each mode is selected using command data that programs the stimulator system to operate in the respective mode, the processor comprising:
        memory containing the command data and non-parametric waveform data representing at least one waveform preprogrammed to achieve electrical stimulation of a brain; and
        a playback system programmed to retrieve the processed non-parametric data representing the at least one preprogrammed waveform from the memory and to play back a composite waveform combined from at least two of the retrieved at least one preprogrammed waveform; and
    at least one electrode in electrical communication with the playback system and programmed to receive the composite waveform and deliver an electrical pulse to stimulate the brain using the composite waveform,
    wherein responsive to first command data corresponding to a first mode, the processor stores non-parametric waveform data received by a data bus into the memory, wherein responsive to second command data corresponding to a second mode, the processor selectively retrieves the at least one of the stored waveform representations from the memory to provide to the playback system.

41. The implantable programmable stimulator system of claim 40, wherein responsive to third command data corresponding to a third mode, the processor obtains feedback diagnostic information about the system.

* * * * *